United States Patent
Or et al.

(10) Patent No.: US 6,462,026 B1
(45) Date of Patent: Oct. 8, 2002

(54) BICYCLIC LEUCOMYCINS

(75) Inventors: Yat Sun Or, Cambridge, MA (US); Sophie Binet, Roslindale, MA (US); Ly Tam Phan, Malden, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 09/785,727

(22) Filed: Feb. 16, 2001

(51) Int. Cl.[7] .................... A61K 31/70; C07M 17/08
(52) U.S. Cl. .................... 514/30; 514/28; 536/7.1
(58) Field of Search ........................ 536/7.1; 514/28, 514/30

(56) References Cited

U.S. PATENT DOCUMENTS

| | | | |
|---|---|---|---|
| 4,820,694 A | 4/1989 | Debono et al. | 514/30 |
| 5,140,014 A | 8/1992 | Maring et al. | 514/30 |
| 5,716,939 A | 2/1998 | Lundy et al. | 514/30 |
| 5,760,011 A | 6/1998 | Jaynes et al. | 514/30 |

FOREIGN PATENT DOCUMENTS

| | | | |
|---|---|---|---|
| WO | PCT/IB94/00199 | 1/1995 | C07D/407/12 |

*Primary Examiner*—Elli Peselev
(74) *Attorney, Agent, or Firm*—Gaetano D. Maccarone, Esq.

(57) ABSTRACT

Bicyclic leucomycins and pharmaceutically acceptable compositions comprising a therapeutically effective amount of a compound of the invention in combination with a pharmaceutically acceptable carrier, a method for treating bacterial infections by administering to a mammal a pharmaceutical composition containing a therapeutically-effective amount of a compound of the invention, and processes for the preparation of such compounds.

15 Claims, No Drawings

BICYCLIC LEUCOMYCINS

TECHNICAL FIELDS

The present invention relates to novel leucomycins having antibacterial activity and useful in the treatment and prevention of bacterial infections. More particularly, the invention relates to bicyclic leucomycins, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Natural macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin and josamycin.

The 16-membered ring macrolide antibiotics constitute an important clinically useful series of naturally occurring compounds within the macrolide class of antibiotics, as they show some advantages over 14-membered ring compounds (gastrointestinal tolerance and activity against strains expressing resistance of the inducible type. Sixteen membered macrolides usually contain an amino disaccharide -4-O-(L-mycarosyl)-D-mycaminose and/or D-desosamine. One class has only neutral sugars. The sixteen membered macrolides can be classified into two major groups—the leucomycins and the tylosin series.

The leucomycins, represented by Formulas Ia and Ib, are further divided, as follows, into five groups according to the chromophores:

(Ia)

(Ib)

1. Leucomycin group containing platenomycin A1, A0 and C2, josamycin (leucomycin A3) and midecamycin A1 and A2.
2. Maridomycin group containing platenomycin C1.
3. Carbomycin B group containing platenomycin W1, midecamycin A4 and A3 and niddamycin
4. Carbomycin A group containing the deltamycin complex
5. Spiramycin complex.

The leucomycins, carbomycins, maridomycins, platenomycins, midecamycins and spiramycins are members of the magnamycin group of 16-membered macrolides, having D-mycaminose and L-mycarose as sugar moieties and an aglycone with an identical carbon skeleton. The antibiotics differ from each other in terms of the acyl group on positions O-3 and O-4" and the C12, 13 epoxy group. Within a given chromophoric group, it is possible to differentiate the various compounds by the substituent at C-3 and C-4".

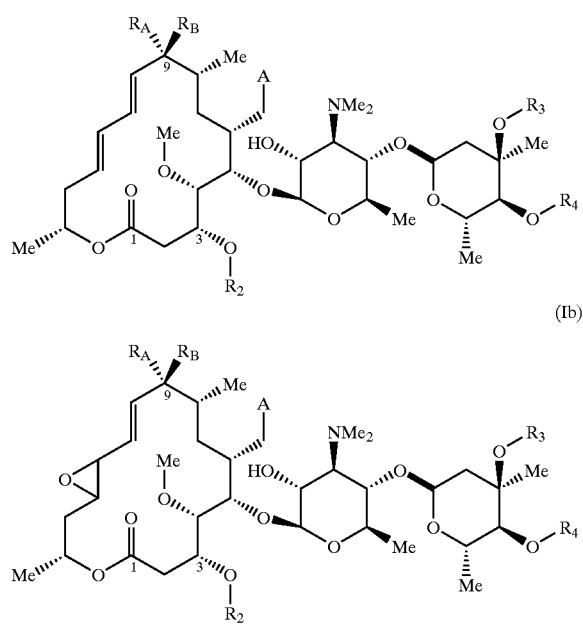

| Leucomycin | R2 | R4 |
|---|---|---|
| A1 | H | C(O)CH2CHMe2 |
| (Kitasamycin) A5 | H | C(O)CH2CH2CH3 |
| A7 | H | C(O)CH2CH3 |
| A9 | H | C(O)CH3 |
| V(A11) | H | H |
| (Josamycin) A3 | C(O)CH3 | C(O)CH2CHMe2 |
| A4 | C(O)CH3 | C(O)CH2CH2CH3 |
| A6 | C(O)CH3 | C(O)CH2CH3 |
| A8 | C(O)CH3 | C(O)CH3 |
| U | C(O)CH3 | H |
| Miokamycin[1] | C(O)CH2CH3 | C(O)CH2CH2CH3 |
| Rokitamycin[2] | H | C(O)CH2CH2CH3 |

[1] 9-OAc; 3"-OAc
[2] 3"-OC(O)CH2CH3; 4"-OC(O)CH2CH2CH3

Josamycin is produced by *Streptomyces narbonensis* var. *josamyceticus*. Josamycin was found to be identical to leucomycin A3. Josamycin belongs to the leucomycin Ac group and differs from the other members by the 4"-O-substituent. Josamycin has a 4"-O-isovaleryl side-chain. In acidic aqueous solution, josamycin is transformed into isojosamycin (isoleucomycin A3) in which the hydroxyl group at C-13 is transferred from C-9. Four metabolites have been isolated from the urine and plasma of adults given oral josamycin. Two show poor antimicrobial activity [(5-hydroxyjosamycin ($O_1$) and β-hydroxyisovaleryl josamycin ($O_2$)] and two are inactive (desisovaleryl josamycin and demycarosyl josamycin or josambose). The pediatric formulation is josamycin propionate.

Leucomycin A5 is one of the components of the leucomycin complex named kitasamycin, and is produced from the fermentation broth of a strain of *Streptomyces kitasatoensis*. It was obtained as a single component by controlling the culture conditions.

Rokitamycin is a semisynthetic 16-membered-ring macrolide obtained by attaching a propionate to the 3"-position of leucomycin A5. 3"-O-propionyl leucomycin A5 is the most active derivative of 3"-O-butyryl derivatives and shows the highest serum levels in dogs and monkeys. The 3"-O-acetyl and 3"-O-butyryl derivatives were less active than 3"-O-propionyl leucomycin A5.

The in vitro activity of rokitamycin against Gram-negative bacteria is twice as high as that of leucomycin A5, josamycin, and midecamycin. Rokitamycin is highly metabolized into four metabolites—10"-hydroxyrokitamycin, leucomycin A7, leucomycin V and 14-hydroxyleucomycin V. Leucomycin A7 and Lecomycin V (4"-debutyryl leucomycin A5) are the main metabolites. Their in vitro potency is respectively one-half and one-tenth that of the parent compound.

Midecamycins are fermentation products of *Streptomyces mycarofaciens* and include four components—A1, A2, A3, and A4. Midecamycin A1 and A2 belong to chromophoric group I, and midecamycin A3 and A4 to chromophoric group III.

Midecamycin A2, A3 and A4 are minor components of the mixture produced by *Streptomyces mycarofaciens*; the major component, A1, has been marketed.

Miokamycin is a semisynthetic 16-membered-ring macrolide derived from midecamycin A1 by introducing two acetyl groups at C-3" and C-9. A large number of acyl derivatives has been prepared by modifying the hydroxyl groups at C-9, C-2' and C-3" of midecamycin A1, in order to improve the biological activities and pharmaceutical properties.

Platenomycins were isolated from the fermentation broth of *Streptomyces platensis* MCRL 0388. Platenomycin complex is composed of nine components—A$_o$, (YL-7$_{04}$), A1 (turimycin P5), B1, C1, C2 (espinomycin A3), C4 (maridomycin II), W1, W2 and W3. The chemical structure of the different compounds has been elucidated. Platenomycin C1 was found to be identical to maridomycin III, and platenomycin B1 to midecamycin III, and platenomycin B1 to midecamycin and espinomycin A1.

Platenomycin has a 16-membered-ring lactone, one aminosugar (D-mycaminose) and one neutral sugar (L-mycarose).

The members of platenomycin complex can be differentiated by the aglycone moiety: platenolide I has a 9-hydroxyl (platenomycins W1, W2).

Carbomycin was isolated from the fermentation broth of *Streptomyces halstedii*. The carbomycin complex has two components—carbomycin A and carbomycin B.

Carbomycin A is identical to deltamycin A4. Carbomycin B (magnamycin B) is used in veterinary medicine.

Niddamycin was isolated from the fermentation broth of a strain of *Streptomyces djaktensis*. It is a substituted 16-membered lactone with an amino sugar (D-mycaminose) and a neutral sugar (L-mycarose). The D-mycaminose is bound to C-5 of the aglycone nucleus, while the L-mycarose (substituted at C-4" with an isovaleryl) binds to the C-4' hydroxyl of D-mycaminose. The lactone ring has a C-6 formylmethyl group. It has no acetyl group at C-3.

Niddamycin shows good antibacterial activity in vitro against Gram-positive bacteria and Mycoplasma spp.

Spiramycin complex consists of three major (I, II, III) and three minor components (IV, V, VI). They were derived from the fermentation broth of *Streptomyces ambofaciens*, a soil organism isolated in the north of France.

Spiramycins consist of four structural components—a 16-membered lactone (platenolide), two amino sugars (D-mycaminose and D-forosamine) and one neutral sugar (L-mycarose). Of the 16-membered-ring macrolide antibiotics, only the spiramycins bear D-forosamine. This amino-sugar is attached to position 9 of the platenolide ring. The three major components differ by the substituent at position 3, as follows: spiramycin I (3-OH), spiramycin II (3-O-acetyl) and spiramycin III (3-O-propionyl). Spiramycin IV and spiramycin VI have a secondary alcohol at C-6 instead of a formylmethyl group. Spiramycin V differs from spiramycin I by the presence of an L-mycarose instead of a D-forosamine. Spiramycin IV bears a D-forosamine and spiramycin VI an L-mycarose.

The antibacterial spectrum of the spiramycins is similar to that of other macrolide antibiotics. They are less active than erythromycin A and show antiprotozoal activity. After oral intake, a certain proportion of spiramycin is demycarsolated into neospiramycin in the stomach.

The search for macrolides active against MLS-resistant strains (MLS=Macrolides-Lincosamides-Streptogramines) has become a major goal, together with retaining the overall profile of the macrolides in terms of stability, tolerance and pharmacokinetics. Semisynthetic molecules have recently been developed from erythromycin A; new compounds containing a 14-membered lactone ring with chemical modifications to enhance acid stability and prevent anhydro formation include roxithromycin and clarithromycin.

However, less research has been done to improve the sixteen membered macrolides to overcome resistance.

SUMMARY OF THE INVENTION

The present invention provides a novel class of bicyclic leucomycins possessing antibacterial activity toward Gram positive and Gram negative bacteria as well as macrolide resistant Gram positives.

In one embodiment, the present invention provides compounds represented by Formulas II, III, IV or V, or a pharmaceutically acceptable salt, ester or prodrug thereof:

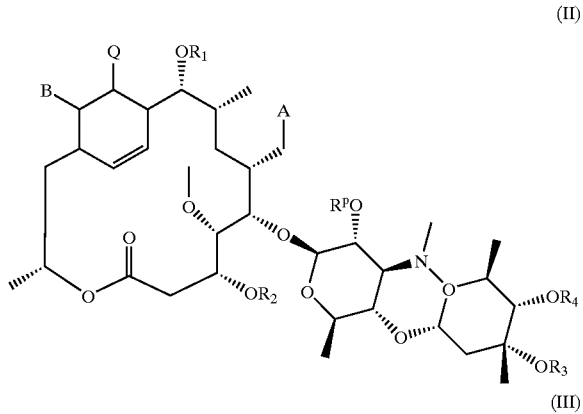

(II)

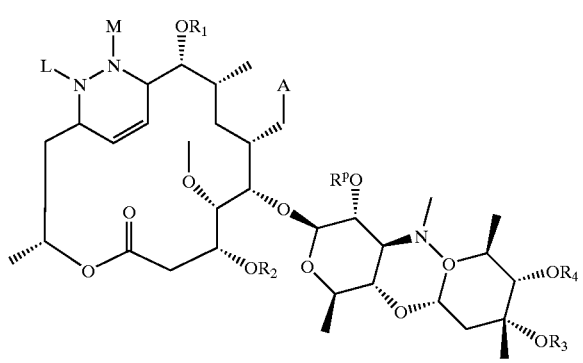

(III)

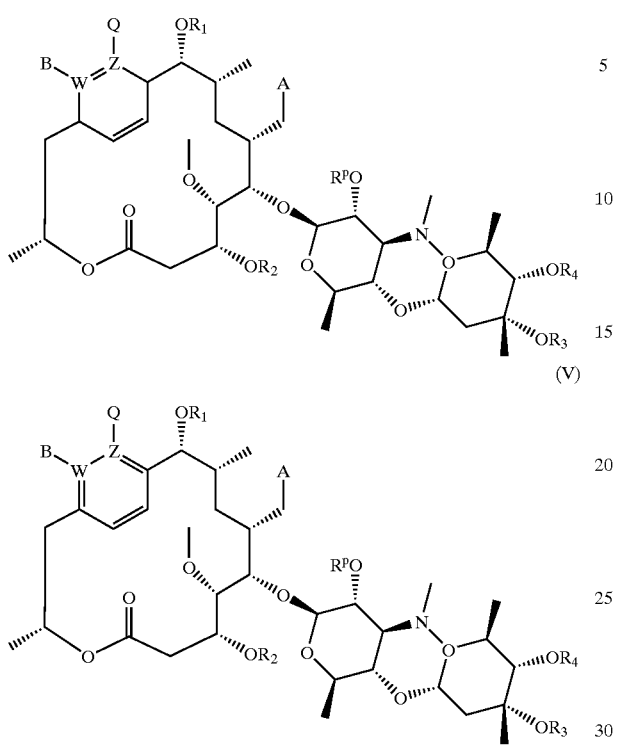

In Formulas II–V:

A is selected from the group consisting of;
(1) —CHO or a protected aldehyde,
(2) —CH2X, wherein X is selected from the group consisting of;
  a. hydroxy or protected hydroxy,
  b. halogen,
  c. —NR7R8 wherein R7 and R8 are each independently selected from hydrogen, aryl, heterocyclic, substituted aryl, substituted heterocyclic, C1–C6-alkyl, optionally substituted with aryl, substituted aryl, heterocyclic or substituted heterocyclic, C2–C6-alkenyl, optionally substituted with aryl, substituted aryl, heterocyclic or substituted heterocyclic and C2–C6-alkynyl, optionally substituted with aryl, substituted aryl, heterocyclic or substituted heterocyclic, or R7R8 taken with the nitrogen atom to which they are connected form a 3- to 7-membered ring which, may optionally contain a hetero function selected from the group consisting of —O—, —NH—, —N(C1–C6-alkyl)-, —N(aryl)-, —N(heteroaryl)—, —S—, —S(O)— and —S(O)2—,
  d. —NR7C(O)—R9, where R7 is as previously defined and R9 is selected from the group consisting of;
    i. C1–C6-alkyl, optionally substituted with aryl, substituted aryl, heterocyclic or substituted heterocyclic,
    ii. C2–C6-alkenyl, optionally substituted with aryl, substituted aryl, heterocyclic or substituted heterocyclic,
    iii. C2–C6 alkynyl, optionally substituted with aryl, substituted aryl, heterocyclic or substituted heterocyclic,
    iv. aryl,
    v. substituted aryl,
    vi. heterocyclic, and
    vii. substituted heterocyclic
  e. —NR7C(O)—NR8R9, where R7, R8, and R9 are as previously defined,
  f. —S(O)$_n$—(C1–C6-alkyl), optionally substituted with aryl, substituted aryl, heterocyclic or substituted heterocyclic where n=0, 1 or 2,
  g. —S(O)$_n$—(C2–C6-alkenyl), optionally substituted with aryl, substituted aryl, heterocyclic or substituted heterocyclic, where n is as previously defined,
  h. —S(O)$_n$—(C2–C6-alkynyl), optionally substituted with aryl, substituted aryl, heterocyclic or substituted heterocyclic, where n is as previously defined,
  i. —S(O)$_n$—(aryl or heterocyclic) where n is as previously defined,
  j. —O—(aryl or heterocyclic),
  k. —O—(C1–C6-alkyl), optionally substituted with aryl, substituted aryl, heterocyclic or substituted heterocyclic,
  l. —O—(C2–C6-alkenyl), optionally substituted with aryl, substituted aryl, heterocyclic or substituted heterocyclic, and
  m. —O—(C2–C6-alkynyl), optionally substituted with aryl, substituted aryl, heterocyclic or substituted heterocyclic,
(3) substituted or unsubstituted imidazole, arylimidazole or heteroarylimidazole,
(4) substituted or unsubstituted oxazole, aryloxazole or heteroaryloxazole,
(5) substituted or unsubstituted thioxazole, arylthioxazole or heteroarylthioxazole,
(6) substituted or unsubstituted imidazoline, arylimidazoline or heteroarylimidazoline,
(7) substituted or unsubstituted oxazoline, aryloxazoline or heteroaryloxazoline, and
(8) substituted or unsubstituted thioxazoline, arylthioxazoline and heteroarylthioxazoline,
  W and Z are each independently selected from the group consisting of carbon and nitrogen,
  B and Q are each independently selected from the group consisting of;
(1) hydrogen
(2) —C(O)OR7 where R7 is as previously defined,
(3) —C(O)R7 where R7 is as previously defined,
(4) —C(O)NR7R8 where R7 and R8 are as previously defined,
(5) —CH2X, where X is as previously defined,
(6) —CN,
(7) —CHO,
(8) C1–C6-alkyl, optionally substituted with R9 where R9 is as previously defined,
(9) C2–C6-alkenyl, optionally substituted with R9 where R9 is as previously defined,
(10) C2–C6-alkynyl, optionally substituted with R9 where R9 is as previously defined, and
(11) B and Q are taken together to form
  a. —C(O)OC(O)—, or
  b. —C(O)YC(O)—, where Y is selected from the group consisting of;
    i. C1–C6 alkyl, optionally substituted with R7 where R7 is as previously defined, ii. C2–C6 alkenyl, optionally substituted with R7 where R7 is as previously defined, and iii. —NR7—, where R7 is as previously defined, provided that in Formulas IV and V, B is absent when W is nitrogen, and Q is absent when Z is nitrogen, L and M are each independently selected from the group consisting of;

(1) hydrogen,
(2) —C(O)OR7, where R7 is as previously defined,
(3) —C(O)R7, where R7 is as previously defined,
(4) —C(O)NR7R8, where R7 and R8 are as previously defined,
(5) —CHO,
(6) C1–C6-alkyl, optionally substituted with R9, where R9 is as previously defined,
(7) —CH2—(C2–C6-alkenyl), optionally substituted with R9, where R9 is as previously defined,
(8) —CH2—(C2–C6-alkynyl), optionally substituted with R9, where R9 is as previously defined, and
(9) L and M are taken together to form —C(O)YC (O)—, where Y is as previously defined, R1 and R2 are each independently selected from the group consisting of;

(1) hydrogen,
(2) hydroxy,
(3) protected hydroxy,
(4) —OC(O)—(C1–C12-alkyl), optionally substituted with aryl, substituted aryl, heterocyclic, substituted heterocyclic, —O—R7 or —NR7R8 where R7 and R8 are as previously defined,
(5) D-forosamine and
(6) L-mycarose R3 and R4 are each independently selected from the group consisting of;

(1) hydrogen,
(2) a hydroxy protecting group,
(3) —C(O)—(C1–C12-alkyl), optionally substituted with aryl, substituted aryl, heterocyclic, substituted heterocyclic, —O—R7 or —NR7R8 where R7 and R8 are as previously defined, and $R^P$ is hydrogen or a hydroxy protecting group.

In another embodiment, the present invention provides a process for preparing novel bicyclic compounds represented by Formulas II, III, IV or V, wherein the groups A, B, L, M, Q, W, Z, R1, R2, R3, R4, and $R^P$ are previously defined.

DETAILED DESCRIPTION OF THE INVENTION

A first embodiment of the invention is a compound represented by Formula II as described above.

A second embodiment of the invention is a compound represented by Formula III as described above.

A third embodiment of the invention is a compound represented by Formula IV as described above.

A fourth embodiment of the invention is a compound represented by Formula V as described above.

Representative compounds of the invention are those selected from the group consisting of:

Compound of Formula III: A=CHO, R1=H, R2=Ac, R3=H, R4=C(O)CH2CHMe2, $R^P$=H, L and M taken together are —C(O)N(Ph)C(O)—

Compound of Formula III: A=CHO, R1=H, R2=Ac, R3=H, R4=C(O)CH2CHMe2, $R^P$=H, L and M taken together are —C(O)NCH$_3$C(O)—

Compound of Formula II: A=CHO, R1=H, R2=Ac, R3=H, R4=C(O)CH2CHMe2, $R^P$=H, B and Q taken together are —C(O)N(Ph)C(O)—

Compound of Formula II: A=CHO, R1=H, R2=Ac, R3=H, R4=C(O)CH2CHMe2, $R^P$=H, B and Q taken together are —C(O)NHC(O)—

Compound of Formula II: A=CHO, R1=H, R2=Ac, R3=H, R4=C(O)CH2CHMe2, $R^P$=H, B and Q taken together are —C(O)OC(O)—

Compound of Formula II: A=CHO, R1=H, R2=Ac, R3=H, R4=C(O)CH2CHMe2, $R^P$=H, B and Q taken together are —C(O)CH=CHC(O)—

Compound of Formula III: A=CHO, R1=Ac, R2=Ac, R3=H, R4=C(O)CH2CHMe2, $R^P$=H, L and M taken together are —C(O)N(Ph)C(O)—

Compound of Formula II: A=CHO, R1=D-forosamine, R2=Ac, R3=H, R4=H, $R^P$=H, B and Q taken together are —C(O)OC(O)—

Compound of Formula II: A=CHO, R1=D-forosamine, R2=propionyl, R3=H, R4=H, $R^P$=H, B and Q taken together are —C(O)OC(O)—

Compound of Formula II: A=CHO, R1=D-forosamine, R2=Ac, R3=H, R4=H, $R^P$=H, B and Q taken together are —C(O)N(Ph)C(O)—

Compound of Formula II: A=CHO, R1=D-forosamine, R2=propionyl, R3=H, R4=H, $R^P$=H, B and Q taken together are —C(O)N(Ph)C(O)—

Compound of Formula IV: A=CHO, R1=H, R2=Ac, R3=H, R4=C(O)CH2CHMe2, $R^P$=H, W=Z=C, B=H, Q=CN Compound of Formula V: A=CHO, R1=H, R2=Ac, R3=H, R4=C(O)CH2CHMe2, $R^P$=H, W=Z=C, B=H, Q=CN Compound of Formula IV: A=CHO, R1=H, R2=H, R3=H, R4=C(O)CH2CH2CH3, $R^P$=H, W=Z=C, B=H, Q=CN Compound of Formula V: A=CHO, R1=H, R2=H, R3=H, R4=C(O)CH2CH2CH3, $R^P$=H, W=Z=C, B=H, Q=CN Compound of Formula III: A=CHO, R1=H, R2=H, R3=H, R4=C(O)CH2CH2CH3, $R^P$=H, L and M taken together are —C(O)N(Ph)C(O)—

Compound of Formula III: A=CHO, R1=H, R2=H, R3=H, R4=C(O)CH2CH2CH3, $R^P$=H, L and M taken together are —C(O)NCH3C(O)—

Compound of Formula II: A=CHO, R1=H, R2=H, R3=H, R4=C(O)CH2CH2CH3, $R^P$=H, B and Q taken together are —C(O)N(Ph)C(O)—

Compound of Formula II: A=CHO, R1=H, R2=H, R3=H, R4=C(O)CH2CH2CH3, $R^P$=H, B and Q taken together are —C(O)NHC(O)—

Compound of Formula II: A=CHO, R1=H, R2=H, R3=H, R4=C(O)CH2CH2CH3, $R^P$=H, B and Q taken together are —C(O)OC(O).

Compound of Formula II: A=CHO, R1=H, R2=H, R3=H, R4=C(O)CH2CH2CH3, $R^P$=H, B and Q taken together are —C(O)CH=CHC(O)— and Compound of Formula III: A=CHO, R1=Ac, R2=H, R3=H, R4=C(O)CH2CH2CH3, $R^P$=H, L and M taken together are —C(O)N(Ph)C(O)—.

Definitions

The terms "$C_1$–$C_3$-alkyl" or "$C_1$–$C_6$-alkyl" as used herein refer to saturated, straight- or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_1$–$C_6$-alkoxy" as used herein refers to a $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, isopropoxy, n-butoxy, tert-butoxy, neopentoxy and n-hexoxy.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methylpyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl" as used herein refers to unsubstituted carbocyclic aromatic groups including, but not limited to, phenyl, 1- or 2-naphthyl and the like.

The term "$C_3$–$C_5$-cycloalkyl- and $C_3$–$C_7$-cycloalkyl" as used herein refers to carbocyclic groups of 3 to 5 or 3 to 7 carbon atoms, respectively, such as for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic 5-, 6- or 7- membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic, as used herein, refers to heterocycloalkyl and heteroaryl. The term "substituted heterocyclic", as used herein, refers to substituted heterocycloalkyl and substituted heteroaryl.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "substituted aryl" as used herein refers to an aryl group as defined herein substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl" as used herein refers to a heteroaryl group as defined herein substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heterocycloalkyl" as used herein, refers to a heterocycloalkyl group, as defined above, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a microdilution method. Minimal Inhibitory Concentration (MIC) was determined in 96 well microtiter plates utilizing the appropriate Mueller Hinton Broth medium (CAMHB) for the observed bacterial isolate.

Antimicrobial agents were serially diluted (2-fold) in DMSO to produce a concentration range of 32 µg/ml to 0.0625 µg/ml. The diluted compounds (2 µl/well) were then transferred into sterile, uninoculated CAMHB 0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 µl/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC.

Antibiotic control standards were included in alternate wells of the same 96 well plate as the antimicrobial agent of interest for testing. The selected control agent was chosen as a compound belonging to the same antibiotic class as the test compound and having known susceptibility patterns for the bacterial organism being tested.

All in vitro testing followed the guidelines described in the Approved Standards M7-A4 protocol published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulate matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: AIBN for azobisisobutyronitrile; $Bu_3SnH$ for tributyltin hydride; CDI for carbonyldiimidazole; DBU for 1,8-diazabicyclo[5.4.0] undec-7-ene; DEAD for diethylazodicarboxylate; DMF for dimethyl formamide; DPPA for diphenylphosphoryl azide; EtOAc for ethyl acetate; MeOH for methanol; $NaN(TMS)_2$ for sodium bis(trimethylsilyl)amide; NMO for N-methylmorpholine N-oxide; TEA for triethylamine; THF for tetrahydrofuran; TPP for triphenylphosphine; DMAP for 4-N,N-dimethylamino pyridine; and TFA for trifluoroacetic acid.

Synthetic Methods

The compounds and processes of the present invention will be better understood in connection with the following synthetic schemes which are illustrative of the methods by which the compounds of the invention may be prepared. The groups A, B, L, M, Q, W, Z, R1, R2, R3, R4, and $R^P$ are as defined previously unless otherwise noted below.

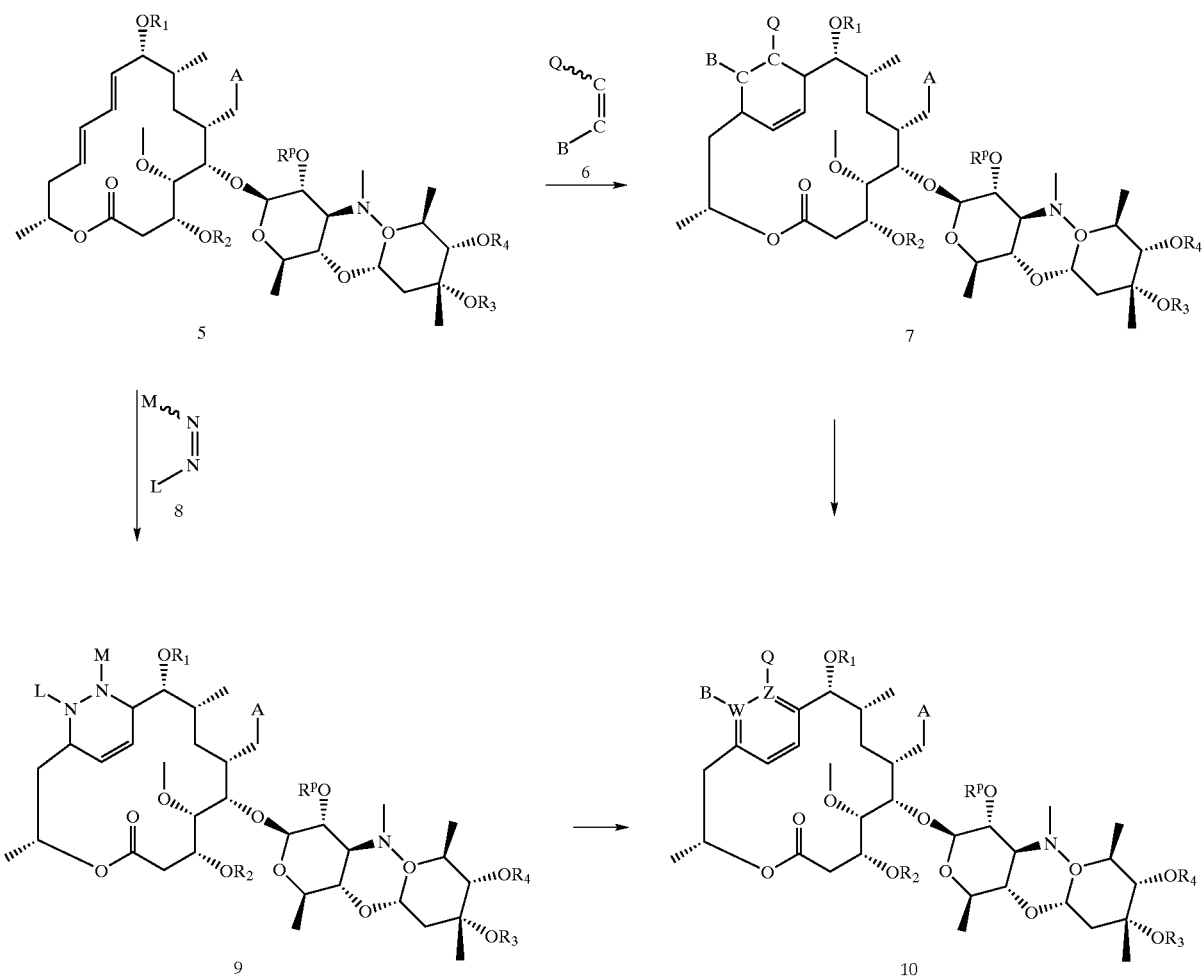
Scheme 1
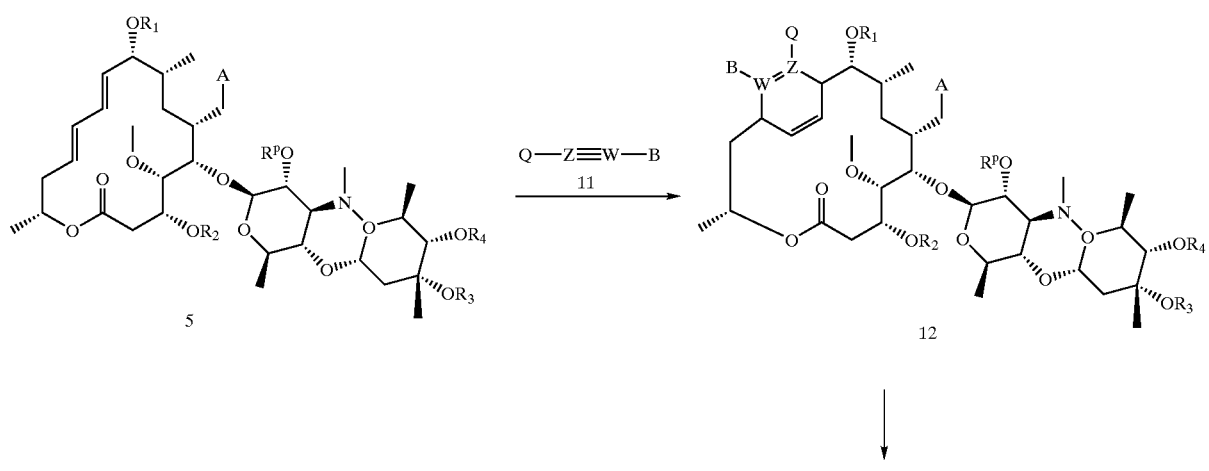
Scheme 2

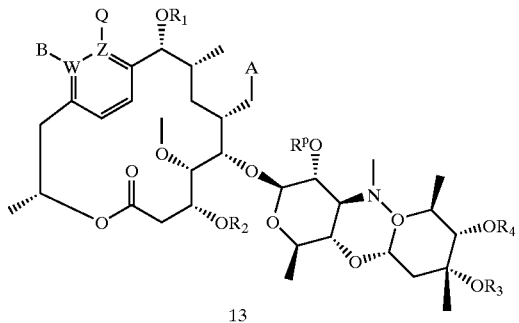

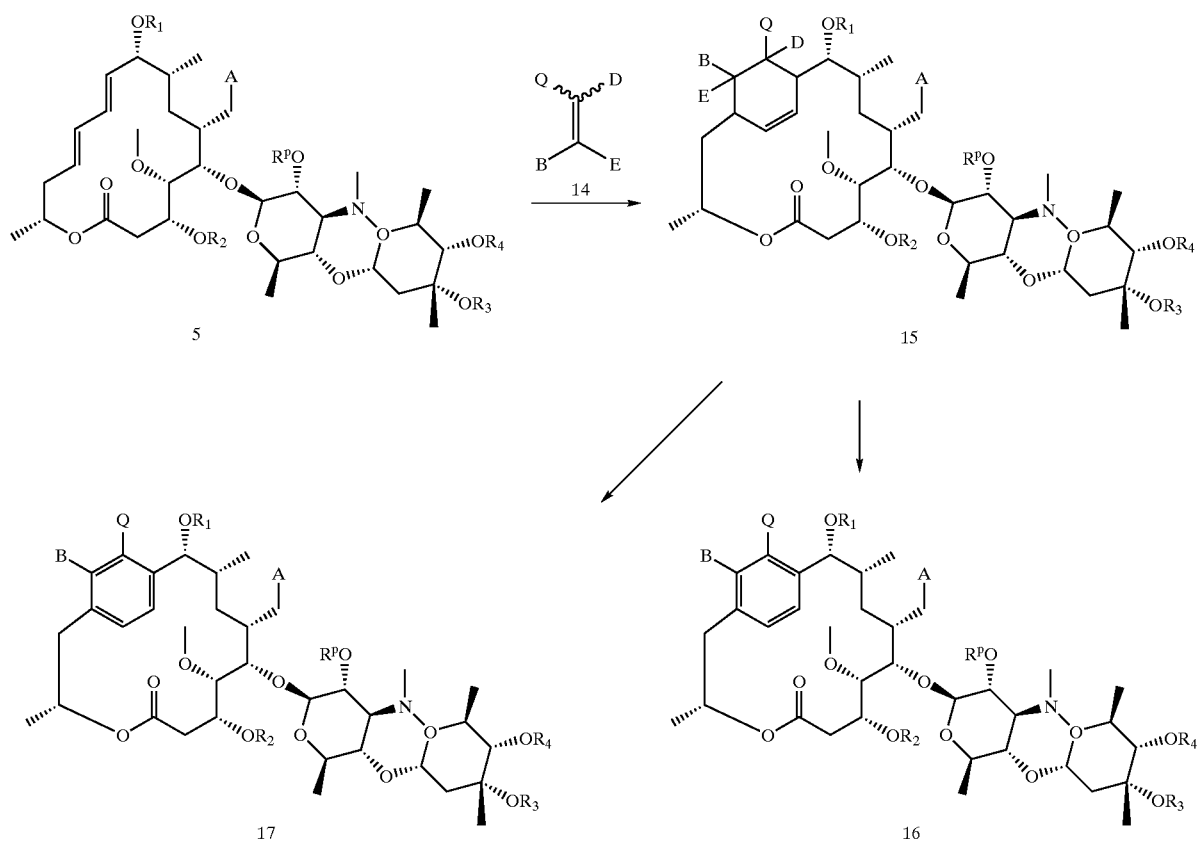

Scheme 3

One process of the invention for the preparation of the compounds of Formulas II and III comprises reacting compound 5 of Scheme 1 wherein A, R1, R2, R3, R4, and $R^P$ are as previously defined, with a dienophile 6 or 8 of Scheme 1 wherein B, Q, L and M are as previously defined, in an organic solvent such as toluene, benzene, acetonitrile, xylene, THF, DMF and the like or neat without solvent at room temperature to about 250° C. to provide compound 7 (Formula II) or 9 (Formula III) of Scheme 1. Additives such as $LiClO_4$, $BF_3 \cdot Et_2O$, $Et_2AlCl$, $TiCl_4$, $Ti(O^iPr)_4$, RhCl $(PPh_3)_3$ and the like which enhance the rate of the Diels-Alder reactions can be optionally added. Compounds 7 and 9 are further oxidized to compound 10 (Formula V) by a variety of oxidation methods and reagents including but not limited to: 1) oxidizing reagents such as DDQ, $KMnO_4/Al_2O_3$, $MnO_2$, and the like in organic solvents such as benzene, acetone, acetonitrile, chloroform, methylene chloride, THF, dioxane, and the like at from room temperature to about 110° C.; 2) treating compound 7 or 9 with a base such as $K_2CO_3$, $Na_2CO_3$, NaOH, $KO^tBU$, and the like in the presence of air or oxygen in an organic solvent such as THF, methylene chloride, DMF, DMSO and the like at from room temperature to about 60° C.; 3) treating compound 7 or 9 with palladium on carbon neat or in organic solvents such as nitrobenzene, toluene and the like at from about 100 to about 250° C.

Another process of the invention for the preparation of compounds of Formulas IV and V comprises reacting compound 5 of Scheme 2, wherein A, R1, R2, R3, R4 and $R^P$ are as previously defined, with compound 11 of Scheme 2 wherein B, Q, W and Z are as previously defined to provide compound 12 (Formula IV) of Scheme 2 which can be further oxidized as described above to compound 13 (Formula V) of Scheme 2.

Still another process of the invention for the preparation of compounds of Formulas IV and V comprises reacting compound 5 of Scheme 3, wherein A, R1, R2, R3, R4, and $R^P$ are as defined previously, with a dienophile 14 of Scheme 3 wherein B, and Q, are as defined previously and D and E are each independently selected from a group of leaving groups such as chlorine, bromine, iodine, mesylate, tosylate, acetate and the like or either D or E but not both is hydrogen to provide compound 15 of Scheme 3 which spontaneously eliminates D and E or either D or E, or optionally with the treatment of a base such as DBU, $Na_2CO_3$, triethylamine and the like, to provide compounds of Formula V (compound 16) and Formula IV (compound 17).

EXAMPLES

The procedures described above for preparing the compounds of Formulae II–IV of the present invention will be better understood in connection with the following examples which are intended to be illustrative only of, and not limiting of the scope of the invention. Various changes and modifications to the disclosed embodiments will be apparent to those skilled in the art. Such changes and modifications, including without limitation, those relating to the chemical structures, substituents, derivatives, syntheses, formulations and/or methods of the invention may be made without departing from the spirit of the invention and the scope of the appended claims.

Example 1

Compound of Formula III: A=CHO. R1=H, R2=Ac, R3=H, R4=C(O)CH2CHMe2, $R^P$=H, L and M taken together are —C(O)N(Ph)C(O)—

To a degassed solution of josamycin (5, Scheme 1 where R1 is H, R2 is Ac, R3 is H, R4 is —C(O)CH2CHMe2, $R^P$ is H), (300 mg, 0.36 mmol) in 3 mL of toluene was added 4-phenyl-1,2,4-triazoline-3,5-dione (94 mg, 0.54 mmol) and the reaction mixture was refluxed for 24 to 48 hours. The reaction was monitored by TLC until complete disappearance of josamycin. The toluene was then removed in vacuo and the resulting foam was submitted to purification by column chromatography eluting with 2% methanol: methylene chloride to give the title compound as a colorless foam (354 mg).

MS (ESI) m/z 1004 (M+H)$^+$.

Example 2

Compound of Formula III: A=CHO, R1=H, R2=Ac, R3=H, R4=C(O)CH2CHMe2, $R^P$=H, L and M taken together are —C(O)NCH3C(O)—

The title compound was prepared from josamycin according to the general procedure of Example 1 substituting 4-methyl-1,2,4-triazoline-3,5-dione for 4-phenyl-1,2,4-triazoline-3,5-dione.

MS (ESI) m/z 942 (M+H)$^+$, $^{13}$C NMR (100 MHz, CDCl$_3$) ☐ 201.5, 173.1, 171.0, 170.1, 169.5, 169.2, 167.9, 155.1, 151.3, 132.5, 131.0, 129.7, 128.9, 103.6, 96.9, 82.9, 75.7, 72.9, 71.4, 69.9, 69.5, 68.8, 68.4, 68.2, 63.6, 61.8, 50.9, 43.4, 41.8, 38.8, 30.4, 29.8, 29.0, 25.6, 25.5, 25.4, 23.8, 23.1, 22.6, 22.5, 21.1, 20.7, 19.1, 18.0, 14.2, 11.1.

Example 3

Compound of Formula II: A=CHO, R1=H, R2=Ac, R3=H, R4=C(O)CH2CHMe2, $R^P$ H, B and Q taken together are —C(O)N(Ph)C(O)—

The title compound was prepared from josamycin according to the general procedure of Example 1 substituting N-phenylmaleimide for 4-phenyl-1,2,4-triazoline-3,5-dione.

MS (ESI) m/z 1002 (M+H)$^+$; $^{13}$C NMR (100 MHz, CDCl$_3$) ☐ 201.3, 180.5, 177.2, 173.0, 172.0, 170.3, 169.6, 134.3, 131.7, 131.4, 129.2, 128.9, 128.0, 126.7, 126.2, 103.3, 97.1, 85.73, 77.26, 75.9, 72.9, 71.6, 70.4, 69.8, 69.4, 68.7, 63.6, 62.6, 60.4, 47.4, 43.4, 42.6, 42.1, 41.7, 41.5, 38.9, 38.2, 35.5, 34.8, 25.6, 25.5, 22.5, 21.4, 21.1, 20.9, 18.9, 18.0, 14.3.

Example 4

Compound of Formula II: A=CHO, R1=H, R2=Ac, R3=H, R4=C(O)CH2CHMe2. $R^P$=H, B and Q taken together are —C(O)NHC(O)—

The title compound was prepared from josamycin according to the general procedure of Example 1 substituting maleimide for 4-phenyl-1,2,4-triazoline-3,5-dione.

MS (ESI) m/z 926 (M+H)$^+$; $^{13}$C NMR (100 MHz, CDCl$_3$) ☐ 201.5, 182.1, 179.0, 173.1, 172.1, 170.3, 132.9, 129.4, 103.3, 97.1, 85.6, 76.9, 76.0, 72.9, 71.9, 71.4, 70.6, 69.8, 69.5, 68.8, 63.7, 62.5, 53.6, 48.4, 43.4, 42.9, 42.0, 41.7, 38.8, 38.1, 35.6, 34.5, 31.2, 25.6, 25.5, 22.5, 21.4, 20.9, 18.9, 17.9.

Example 5

Compound of Formula II: A=CHO R1=H, R2=Ac, R3=H, R4=C(O)CH2CHMe2, $R^P$=H, B and Q taken together are —C(O)OC(O)—

The title compound was prepared from josamycin according to the general procedure of Example 1 substituting maleic anhydride for 4-phenyl-1,2,4-triazoline-3,5-dione.

MS (ESI) m/z 927 (M+H)$^+$; $^{13}$C NMR (100 MHz, CDCl$_3$) ☐ 201.9, 178.1, 175.3, 173.12, 172.9, 171.2, 169.1, 136.3, 122.0, 104.2, 97.0, 86.2, 75.8, 72.9, 71.2, 69.5, 68.9, 63.8, 61.8, 53.6, 45.1, 43.4, 42.8, 42.1, 41.7, 39.7, 39.6, 36.2, 33.9, 32.7, 25.7, 25.6, 22.6, 22.5, 21.4, 20.8, 19.0, 18.7, 17.9, 17.8.

Example 6

Compound of Formula II: A=CHO, R1=H, R2=Ac, R3=H, R4=C(O)CH2CHMe2, $R^P$=H, B and Q taken together are —C(O)CH=CHC(O)—

The title compound was prepared from josamycin according to the general procedure of Example 1 substituting 1,4-benzoquinone for 4-phenyl-1,2,4-triazoline-3,5-dione.

MS (ESI) m/z 936 (M+H)$^+$.

Example 7

Compound of Formula III: A=CHO, R1=Ac, R2=Ac, R3=H, R4=C(O)CH2CHMe2, $R^P$=H, L and M taken together are —C(O)N(Ph)C(O)—

Step7a: Compound of Formula III: A=CHO, R1=Ac, R2=Ac, R3=H, R4=C(O)CH2CHMe2, $R^P$=Ac, L and M taken together are —C(O)N(Ph)C(O)—

The title compound was prepared according to the general procedure of Example 1 substituting 2',9-diacetylated josamycin (compound 5 from Scheme 1, where R1 is Ac, R2 is Ac, R3 is H, R4 is —C(O)CH2CHMe2, and $R^P$ is Ac) for josamycin.

MS (ESI) m/z 1087 (M+H)$^+$; $^{13}$C NMR (100 MHz, CDCl$_3$) □ 201.3, 173.0, 171.7, 170.3, 168.9, 168.7, 149.1, 131.3, 129.2, 129.1, 128.3, 126.0, 101.0, 97.1, 76.2, 75.8, 72.9, 71.0, 69.5, 67.8, 63.6, 61.9, 60.5, 54.0, 43.4, 41.8, 41.7, 25.6, 25.4, 22.5, 21.7, 21.3, 21.1, 20.9, 18.8, 18.1, 14.3, 110.4, 101.0, 97.1, 89.0, 84.2, 76.2, 75.8, 72.9, 75.8, 72.9, 71.0, 69.5, 67.8, 63.6, 61.9, 60.5, 54.0, 43.4, 41.8, 41.7, 25.6, 25.4, 22.5, 21.7, 21.3, 21.1, 20.9, 18.8, 18.1, 14.3.

Step7b: Compound of Formula III: A=CHO, R1=Ac, R2=Ac, R3=H, R4=C(O)CH2CHMe2, R$^P$=H, L and M taken together are —C(O)N(Ph)C(O)—

The compound of step 7a was dissolved in methanol and the reaction mixture was stirred at room temperature for 24 hours. Removal of the methanol in vacuo gave the title compound.

MS (ESI) m/z 1046 (M+H)$^+$.

Example 8

Compound of Formula II: A=CHO, R1=D-forosamine, R2=Ac, R3=H, R4=H, R$^P$=H, B and Q taken together are —C(O)OC(O)—

The title compound was prepared according to the general procedure of Example 1 by reacting spiramycin II (compound 5 from Scheme 1, where R1=D-forosamine, R2=Ac, R3=H, R4=H, R$^P$=H) with maleic anhydride.

MS (ESI) m/z 986 (M+H)$^+$.

Example 9

Compound of Formula II: A=CHO, R1=D-forosamine, R2=propionyl, R3=H, R4=H, R$^P$=H, B and Q taken together are —C(O)OC(O)—

The title compound was prepared according to the general procedure of Example 1 by reacting spiramycin III (compound 5 from Scheme 1, where R1=D-forosamine, R2=propionyl, R3=H, R4=H, R$^P$=H) with maleic anhydride.

MS (ESI) m/z 998 (M+H)$^+$.

Example 10

Compound of Formula II: A=CHO, R1=D-forosamine, R2=Ac, R3=H, R4=H, R$^P$=H, B and Q taken together are —C(O)N(Ph)C(O)—

The title compound was prepared according to the general procedure of Example 1 by reacting spiramycin II (compound 5 from Scheme 1, where R1=D-forosamine, R2=Ac, R3=H, R4=H, R$^P$=H) with N-phenylmaleimide.

MS (ESI) m/z 1060 (M+H)$^+$.

Example 11

Compound of Formula II: A=CHO, R1=D-forosamine, R2=propionyl, R3=H, R4=H, R$^P$=H, B and Q taken together are —C(O)N(Ph)C(O)—

The title compound was prepared according to the general procedure of Example 1 by reacting spiramycin III (compound 5 from Scheme 1 where R1=D-forosamine, R2=propionyl, R3=H, R4=H, R$^P$=H) with N-phenylmaleimide.

MS (ESI) m/z 1074 (M+H)$^+$.

Example 12

Compound of Formula IV: A=CHO, R1=H, R2=Ac, R3=H, R4=C(O)CH2CHMe2, R$^P$=H, W=Z=C, B=H, Q=CN Step 12a: Compound 15 of Scheme 3: A=CHO, R1=H, R2=Ac, R3=H, R4=C(O)CH2CHMe2, R$^P$=H, W=Z=C, B=E=H, Q=CN, D=OAc The title compound is prepared according to the general procedure of Example 1 by reacting josamycin (compound 5 from Scheme 1, where R1=H, R2=Ac, R3=H, R4=C(O)CH2CHMe2, R$^P$=H) with 1-cyanovinyl acetate.

Step 12b: Compound of Formula IV: A=CHO, R1=H, R2=Ac, R3=H, R4=C(O)CH2CHMe2, R$^P$=H, W=Z=C, B=H, Q=CN The compound from step 12a is treated with DBU in THF at room temperature for 24 hours to give the title compound.

Example 13

Compound of Formula V: A=CHO, R1=H, R2=Ac, R3=H, R4=C(O)CH2CHMe2. R$^P$=H, W=Z=C, B=H, Q=CN The title compound is prepared by treating the compound of Example 12 with MnO$_2$ in CHCl$_3$ at reflux.

Example 14

Compound of Formula IV: A=CHO, R1=H, R2=H, R3=H, R4=C(O)CH2CH2CH3, R$^P$=H, W=Z=C, B=H, Q=CN Step 14a: Compound 15 of Scheme 3: A=CHO, R1=H, R2=H, R3=H, R4=C(O)CH2CH2 CH3, R$^P$=H, B=E=H, Q=CN, D=OAc The title compound is prepared according to the general procedure of Example 1 by reacting kitasanycin (compound 5, Scheme 1, where R1=H, R2=H, R3=H, R4=C(O)CH2CH2CH3, R$^P$=H) with 1-cyanovinyl acetate.

Step 14b: Compound of Formula IV: A=CHO, R1=H, R2=H, R3=H, R4=C(O)CH2CH2CH3, R$^P$=H, W=Z=C, B=H, Q=CN The compound from step 14a is treated with DBU in THF at room temperature for 24 hours to give the title compound.

Example 15

Compound of Formula V: A=CHO, R1=H, R2=H, R3=H, R4=C(O)CH2CH2CH3, R$^P$=H, W=Z=C, B=H, Q=CN The title compound is prepared by treating the compound of Example 14 with MnO$_2$ in CHCl$_3$ at reflux.

Example 16

Compound of Formula III: A=CHO, R1=H, R2=H, R3=H, R4=C(O)CH2CH2CH3, R$^P$=H, L and M taken together are —C(O)N(Ph)C(O)—

The title compound is prepared according to the general procedure of Example 1 by substituting kitasamycin for josamycin.

Example 17

Compound of Formula III: A=CHO, R1=H, R2=H, R3=H, R4=C(O)CH2CH2CH3, R$^P$=H, L and M taken together are —C(O)NCH3C(O)—

The title compound is prepared according to the general procedure of Example 2 by substituting kitasamycin for josamycin.

Example 18

Compound of Formula II: A=CHO, R1=H, R2=H, R3=H, R4=C(O)CH2CH2CH3. R$^P$=H, B and Q taken together are —C(O)N(Ph)C(O)—

The title compound is prepared according to the general procedure of Example 3 by substituting kitasamycin for josamycin.

Example 19

Compound of Formula II: A=CHO, R1=H, R2=H, R3=H, R4=C(O)CH2CH2CH3. $R^P$=H, B and Q taken together are —C(O)NHC(O)—

The title compound is prepared according to the general procedure of Example 4 by substituting kitasamycin for josamycin.

Example 20

Compound of Formula II: A=CHO, R1=H, R2=H, R3=H, R4=C(O)CH2CH2CH3, $R^P$=H, B and Q taken together are —C(O)OC(O)—

The title compound is prepared according to the general procedure of Example 5 by substituting kitasamycin for josamycin.

Example 21

Compound of Formula II: A=CHO, R1=H, R2=H, R3=H, R4=C(O)CH2CH2CH3, $R^P$=H, B and Q taken together are —C(O)CH=CHC(O)—

The title compound is prepared according to the general procedure of Example 6 by substituting kitasamycin for josamycin.

Example 22

Compound of Formula III: A=CHO, R1=H, R2=H, R3=H, R4=C(O)CH2CH2CH3, $R^P$=H, L and M taken together are —C(O)N(Ph)C(O)—

The title compound is prepared according to the general procedure of Example 7 by substituting kitasamycin for josamycin.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the Formula:

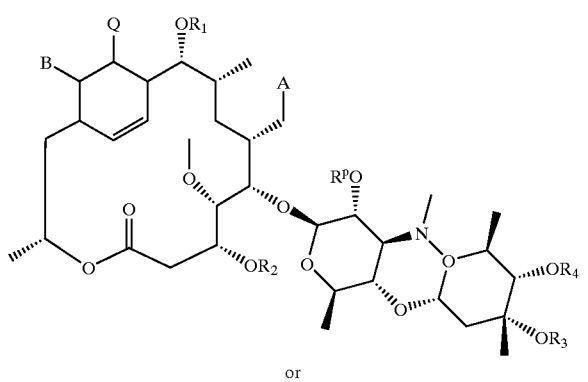

(II)

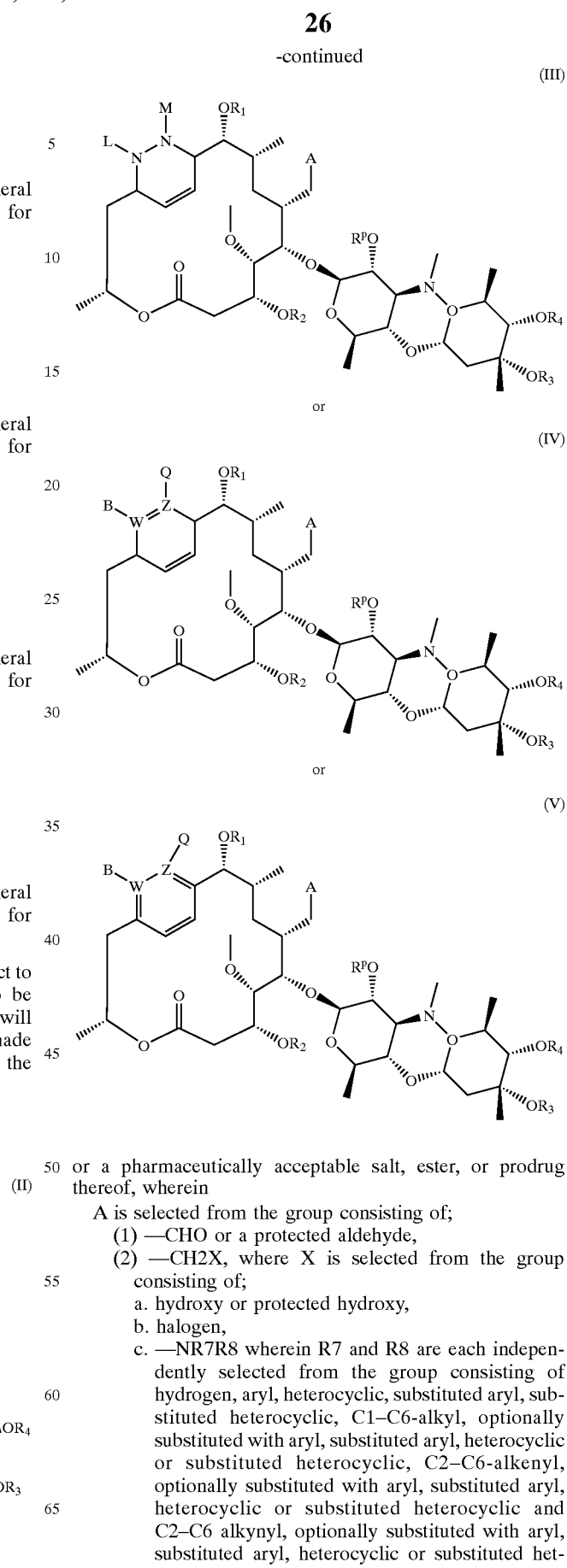

or a pharmaceutically acceptable salt, ester, or prodrug thereof, wherein

A is selected from the group consisting of;
  (1) —CHO or a protected aldehyde,
  (2) —CH2X, where X is selected from the group consisting of;
    a. hydroxy or protected hydroxy,
    b. halogen,
    c. —NR7R8 wherein R7 and R8 are each independently selected from the group consisting of hydrogen, aryl, heterocyclic, substituted aryl, substituted heterocyclic, C1–C6-alkyl, optionally substituted with aryl, substituted aryl, heterocyclic or substituted heterocyclic, C2–C6-alkenyl, optionally substituted with aryl, substituted aryl, heterocyclic or substituted heterocyclic and C2–C6 alkynyl, optionally substituted with aryl, substituted aryl, heterocyclic or substituted heterocyclic; or R7R8 taken with the nitrogen atom to which they are connected form a 3- to 7-membered ring which, may optionally contain a hetero function selected from the group consisting of —O—, —NH—, —N(C1–C6-alkyl)-, —N(aryl)-, —N(heteroaryl)-, —S—, —S(O)— and —S(O)2—,
  d. -NR7C(O)-R9, where R7 is as previously defined, and R9 is selected from the group consisting of;
    i. C1–C6-alkyl, optionally substituted with aryl, substituted aryl, heterocyclic or substituted heterocyclic,
    ii. C2–C6-alkenyl, optionally substituted with aryl, substituted aryl, heterocyclic or substituted heterocyclic,
    iii. C2–C6-alkynyl, optionally substituted with aryl, substituted aryl, heterocyclic or substituted heterocyclic,
    iv. aryl,
    v. substituted aryl,
    vi. heterocyclic, and
    vii. substituted heterocyclic
  e. —NR7C(O)—NR8R9, where R7, R8, and R9 are as previously defined,
  f. —S(O)$_n$—(C1–C6-alkyl), optionally substituted with aryl substituted aryl, heterocyclic or substituted heterocyclic where n=0, 1 or 2,
  g. —S(O)$_n$—(C2–C6-alkenyl), optionally substituted with aryl, substituted aryl, heterocyclic or substituted heterocyclic, where n is as previously defined,
  h. —S(O)$_n$—(C2–C6-alkynyl), optionally substituted with aryl, substituted aryl heterocyclic or substituted heterocyclic, where n=is as previously defined,
  i. —S(O)$_n$—(aryl or heterocyclic) where n is as previously defined,
  j. —O—(aryl or heterocyclic),
  k. —O—(C1–C6-alkyl), optionally substituted with aryl, substituted aryl, heterocyclic or substituted heterocyclic,
  l. —O—(C2–C6-alkenyl), optionally substituted with aryl, substituted aryl, heterocyclic or substituted heterocyclic, and
  m. —O—(C2–C6 alkynyl), optionally substituted with aryl, substituted aryl, heterocyclic or substituted heterocyclic,
(3) substituted or unsubstituted imidazole, arylimidazole or heteroarylimidazole,
(4) substituted or unsubstituted oxazole, aryloxazole or heteroaryloxazole,
(5) substituted or unsubstituted thioxazole, arylthioxazole or heteroarylthioxazole,
(6) substituted or unsubstituted imidazoline, arylimidazoline or heteroarylimidazoline,
(7) substituted or unsubstituted oxazoline, aryloxazoline or heteroaryloxazoline, and
(8) substituted or unsubstituted thioxazoline, arylthioxazoline and heteroarylthioxazoline,
  W and Z are each independently selected from the group consisting of carbon and nitrogen
  B and Q are each independently selected from the group consisting of
(1) hydrogen
(2) —C(O)OR7 where R7 is as previously defined,
(3) —C(O)R7 where R7 is as previously defined,
(4) —C(O)NR7R8 where R7 and R8 are as previously defined,
(5) —CH2X, where X is as previously defined,
(6) —CN,
(7) —CHO,
(8) C1–C6-alkyl, optionally substituted with R9 where R9 is as previously defined,
(9) C2–C6-alkenyl, optionally substituted with R9 where R9 is as previously defined,
(10) C2–C6-alkynyl, optionally substituted with R9 where R9 is as previously defined, and
(11) B and Q are taken together to form
  a. —C(O)OC(O)—, or
  b. —C(O)YC(O)—, where Y is selected from the group consisting of;
    i. C1–C6 alkyl optionally substituted with R7 where R7 is as previously defined,
    ii. C2–C6 alkenyl optionally substituted with R7 where R7 is as previously defined, and
    iii. —NR7—, where R7 is as previously defined,
  provided that in Formulas IV and V, B is absent when W is nitrogen and Q is absent when Z is nitrogen,
  L and M are each independently selected from the group consisting of;
(1) hydrogen,
(2) —C(O)OR7, where R7 is as previously defined,
(3) —C(O)R7, where R7 is as previously defined,
(4) —C(O)NR7R8, where R7 and R8 are as previously defined,
(5) —CHO,
(6) C1–C6-alkyl, optionally substituted with R9, where R9 is as previously defined,
(7) —CH2-(C2–C6-alkenyl), optionally substituted with R9, where R9 is as previously defined,
(8) —CH2—(C2–C6-alkynyl), optionally substituted with R9, where R9 is as previously defined, and
(9) L and M are taken together to form —C(O)YC(O)—, where Y is as previously defined,
  R1 and R2 are each independently selected from the group consisting of
(1) hydrogen,
(2) hydroxy,
(3) protected hydroxy,
(4) —OC(O)—(C1–C12-alkyl), optionally substituted with aryl, substituted aryl, heterocyclic, substituted heterocyclic, —O—R7 or —NR7R8 where R7 and NR7R8 are as previously defined,
(5) D-forosamine, and
(6) L-mycarose
  R3 and R4 are each independently selected from the group consisting of
(1) hydrogen,
(2) a hydroxy protecting group,
(3) —C(O)—(C1–C12-alkyl), optionally substituted with aryl, substituted aryl, heterocyclic, substituted heterocyclic, —O—R7 or —NR7R8 where R7 and R8 are as previously defined; and
  $R^p$ is hydrogen or a hydroxy protecting group.

2. A compound according to claim 1 which is represented by Formula II.

3. A compound according to claim 2 wherein A=CHO, R1=H, R2=Ac, R3=H, R4=C(O)CH2CHMe2, $R^p$=H.

4. A compound according to claim 1 which is represented by Formula III.

5. A compound according to claim 4 wherein A=CHO, R1=H, R2=Ac, R3=H, R4=C(O)CH2CHMe2, $R^p$=H.

6. A compound according to claim 1 which is represented by Formula IV.

7. A compound according to claim 6 wherein A=CHO, R1=H, R2=Ac, R3=H, R4=C(O)CH2CHMe2, $R^p$=H.

8. A compound according to claim 1 which is represented by Formula V.

9. A compound according to claim 8 wherein A=CHO, R1=H, R2=Ac, R3=H, R4=C(O)CH2CHMe2, $R^P$=H.

10. A compound according to claim 1 which is selected from the group consisting of:

Compound of Formula III: A=CHO, R1=H, R2=Ac, R3=H, R4=C(O)CH2CHMe2, $R^P$=H, L and M taken together are —C(O)N(Ph)C(O)—

Compound of Formula III: A=CHO, R1=H, R2=Ac, R3=H, R4=C(O)CH2CHMe2, $R^P$H, L and M taken together are —C(O)NCH3C(O)—

Compound of Formula II: A=CHO, R1=H, R2=Ac, R3=H, R4=C(O)CH2CHMe2, $R^P$H, B and Q taken together are —C(O)N(Ph)C(O)—

Compound of Formula II: A=CHO, R1=H, R2=Ac, R3=H, R4=C(O)CH2CHMe2, $R^P$=H, B and Q taken together are —C(O)NHC(O)—

Compound of Formula II: A=CHO, R1=H, R2=Ac, R3=H, R4=C(O)CH2CHMe2, $R^P$=H, B and Q taken together are —C(O)OC(O)—

Compound of Formula II: A=CHO, R1=H, R2=Ac, R3=H, R4=C(O)CH2CHMe2, $R^P$=H, B and Q taken together are —C(O)CH═CHC(O)—

Compound of Formula III: A=CHO, R1=Ac, R2=Ac, R3=H, R4=C(O)CH2CHMe2, $R^P$=H, L and M taken together are —C(O)N(Ph)C(O)—

Compound of Formula II: A=CHO, R1=D-forosamine, R2=Ac, R3=H, R4=H, $R^P$=H, B and Q taken together are —C(O)OC(O)—

Compound of Formula II: A=CHO, R1=D-forosamine, R2=propionyl, R3=H, R4=H, $R^P$=H, B and Q taken together are —C(O)OC(O)—

Compound of Formula II: A=CHO, R1=D-forosamine, R2=Ac, R3=H, R4=H, $R^P$=H, B and Q taken together are —C(O)N(Ph)C(O)—

Compound of Formula II; A=CHO, R1=D-forosamine, R2=propionyl, R3=H, R4=H, $R^P$=H, B and Q taken together are C(O)N(Ph)C(O)—

Compound of Formula IV: A=CHO, R1=H, R2=Ac, R3=H, R4=C(O)CH2CHMe2, $R^P$=H, W=Z=C, B=H, Q=CN Compound of Formula V: A=CHO, R1=H, R2=Ac, R3=H, R4=C(O)CH2CHMe2, $R^P$=H, W=Z=C, B=H, Q=CN Compound of Formula IV: A=CHO, R1=H, R2=H, R3=H, R4=C(O)CH2CH2CH3, $R^P$=H, W=Z=C, B=H, Q=CN Compound of Formula V: A=CHO, R1=H, R2=H, R3=H, R4=C(O)CH2CH2CH3, $R^P$=H, W=Z=C, B=H, Q=CN Compound of Formula III: A=CHO, R1=H, R2=H, R3=H, R4=C(O)CH2CH2CH3, $R^P$=H, L and M taken together are —C(O)N(Ph)C(O)—

Compound of Formula III: A=CHO, R1=H, R2=H, R3=H, R4=C(O)CH2CH2CH3, $R^P$=H, L and M taken together are —C(O)NCH3C(O)—

Compound of Formula II: A=CHO, R1=H, R2=H, R3=H, R4=C(O)CH2CH2CH3, $R^P$=H, B and Q taken together are —C(O)N(Ph)C(O)—

Compound of Formula II: A=CHO, R1=H, R2=H, R3=H, R4=C(O)CH2CH2CH3, $R^P$=H, B and Q taken together are —C(O)NHC(O)—

Compound of Formula II: A=CHO, R1=H, R2=H, R3=H, R4=C(O)CH2CH2CH3, $R^P$=H, B and Q taken together are —C(O)OC(O)—

Compound of Formula II: A=CHO, R1=H, R2=H, R3=H, R4=C(O)CH2CH2CH3, $R^P$=H, B and Q taken together are —C(O)CH═CHC(O)—, and Compound of Formula III: A=CHO, R1=H, R2=H, R3=H, R4=C(O)CH2CH2CH3, $R^P$=H, L and M taken together are —C(O)N(Ph)C(O)—.

11. A pharmaceutical composition for treating bacterial infections comprising a therapeutically effective amount of a compound of claim 1 or a pharmaceutically acceptable salt, ester or prodrug thereof in combination with a pharmaceutically acceptable carrier.

12. A method for treating bacterial infections comprising administering to a mammal in need of such treatment a pharmaceutical composition containing a therapeutically-effective amount of a compound of claim 1 or a pharmaceutically acceptable salt, ester or prodrug thereof.

13. A process for the preparation of a compound represented by Formulas II–IV as defined in claim 1 comprising reacting a compound represented by the formula

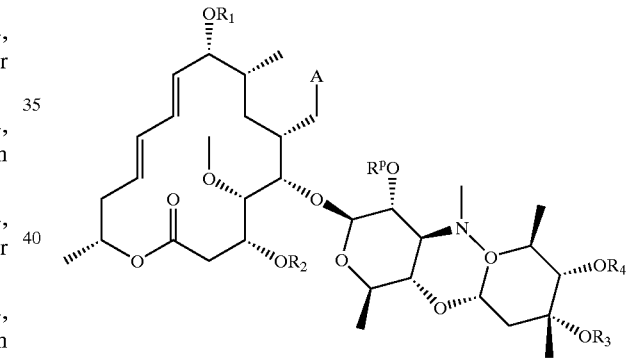

wherein A, R1, R2, R3, R4 and $R^P$ are as defined in claim 1 with a dienophile represented by the formula

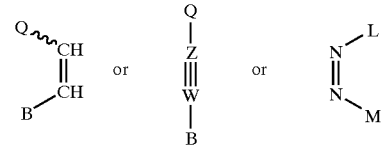

wherein B, Q, W, Z, L and M are as defined in claim 1, optionally in an organic solvent and further optionally in the presence of an additive selected from the group consisting of $LiClO_4$, $BF_3 \cdot Et_2O$, $Et_2AlCl$, $TiCl_4$, $Ti(O^iPr)_4$, and $RhCl(PPh_3)_3$.

14. A process for the preparation of a compound represented by Formula V as defined in claim 1 comprising oxidizing a compound represented by the formula

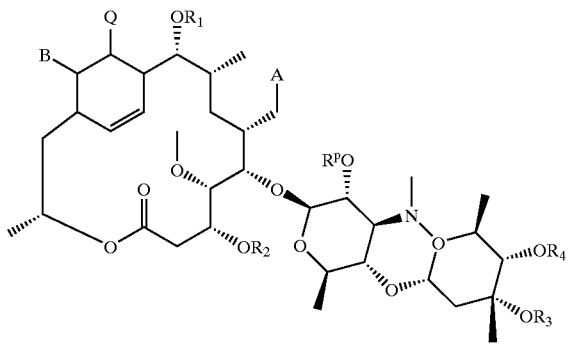

or

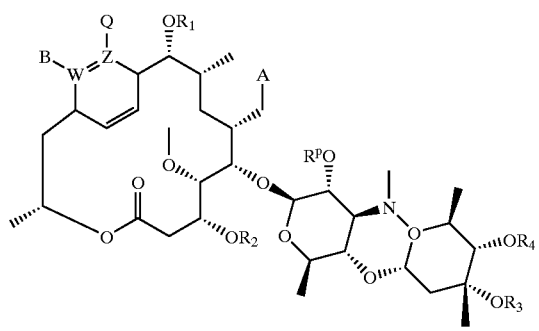

wherein A, B, Q, W, Z, R1, R2, R3, R4 and $R^P$. are as defined in claim 1.

15. A process for the preparation of a compound represented by Formula IV or V as defined in claim 1 comprising reacting a compound represented by the formula

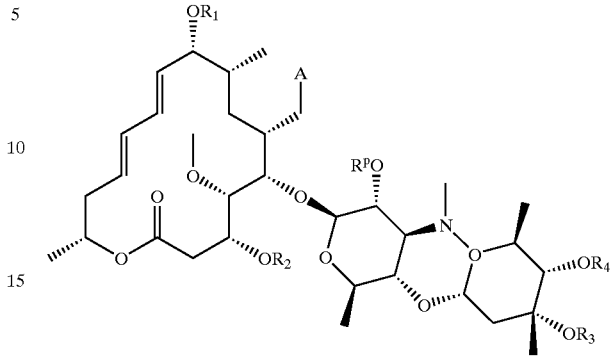

wherein A, R1, R2, R3, R4 and $R^P$ are as defined in claim 1 with a dienophile represented by the formula

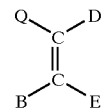

wherein B and Q are as defined in claim 1 and D and E are each independently selected from the group consisting of a leaving group and either D or E but not both is hydrogen.

* * * * *